US00PP12045P2

(12) United States Plant Patent
Osiecki

(10) Patent No.: US PP12,045 P2
(45) Date of Patent: Aug. 7, 2001

(54) ANTHURIUM PLANT NAMED 'ATWENTYONE'

(75) Inventor: Marian W. Osiecki, Marianna, FL (US)

(73) Assignee: Oglesby Plants Intl., Inc., Aliha, FL (US)

( * ) Notice: Subject to any disclaimer, the term of this patent is extended or adjusted under 35 U.S.C. 154(b) by 0 days.

(21) Appl. No.: 09/569,359

(22) Filed: May 11, 2000

(51) Int. Cl.[7] ..... A01H 5/00
(52) U.S. Cl. ..... Plt./369

(58) Field of Search ..... Plt./369, 367

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Anthurium plant named 'Atwentyone', characterized by its dwarf growth habit: high vigor; early and freely flowering habit; large spathes in proportion to the overall plant size; spathes held close to the foliage on relatively strong peduncles; bright red-colored spathes that doesn't fade under conditions of high temperatures and/or high light; and long-lasting spathes.

2 Drawing Sheets

BACKGROUND OF THE INVENTION

The present Invention relates to a new and distinct cultivar of Anthurium plant, botanically known as Anthurium hybrid, and hereinafter referred to by the cultivar name Atwentyone.

The new cultivar is a product of a planned and controlled breeding program conducted by the Inventor in Altha, Fla. The objective of the breeding program is to create dwarf and early-flowering potted anthurium cultivars with attractive spathe color, good spathe longevity, and short production time. The new cultivar originated from a deliberate cross by the Inventor in 1993 between a proprietary Anthurium seedling selection identified as code No. 91-100-2, as the female or seed parent and a proprietary Anthurium seedling selection identified as code No. 91-9-32, as the male or pollen parent. The cultivar Atwentyone was discovered and selected by the Inventor as a plant within the progeny of the stated cross in a controlled environment in Altha, Fla., in 1994.

Asexual propagation of the new cultivar by tissue culture in Altha, Fla., has shown that the unique features of this new Anthurium plant are stable and reproduced true to type in successive generations of asexual propagation.

SUMMARY OF THE INVENTION

The new Anthurium has not been observed under all possible environmental conditions. The phenotype may vary somewhat with variations in environment such as temperature, light intensity, fertilizer rate, irrigation amount and frequency, and/or propagation procedures without, however, and variance in genotype.

The following traits have been repeatedly observed and are determined to be the unique characteristics of 'Atwentyone'. These characteristics in combination distinguish 'Atwentyone' as a new and distinct cultivar:

1. Plants of the new Anthurium have a dwarf growth habit and are suitable for 7.5 to 15-cm containers.
2. Plants of the new Anthurium are vigorous.
3. Plants of the new Anthurium are freely and early flowering.
4. Plants of the new Anthurium have large spathes in proportion to the overall plant size.

5. Spathes of plants of the new Anthurium are held close to the foliage on relatively strong peduncles.
6. Young spathes of plants of the new Anthurium are bright red in color and exceptionally glossy.
7. Bright red spathe color is maintained under conditions of high temperatures and/or high light.
8. Spathes of plants of the new Anthurium are long-lasting. Ornamental value is maintained for several months after maturity.

Plants of the new Anthurium differ from plants of the female parent, the proprietary seedling selection identified as code No. 91-100-2, in the following characteristics:

1. Plants of the new Anthurium have broader leaves than plants of the selection 91-100-2.
2. Plants of the new Anthurium have red-colored spathes whereas plants of the selection 92-100-2 have pink-colored spathes.

Plants of the new Anthurium differ from plants of the male parent, the proprietary seedling selection identified as code No. 91-9-32, in the following characteristics:

1. Plants of the new Anthurium are smaller than plants of the selection 91-9-32.
2. Plants of the new Anthurium have smaller leaves than plants of the selection 91-9-32.
3. Plants of the new Anthurium have smaller spathes than plants of the selection 91-9-32.

Plants of the new Anthurium can be compared to the Anthurium cultivar Atwelve, disclosed in U.S. Plant Patent application Ser. No. 09/292,198. However, in side-by-side comparisons conducted in Altha, Fla., plants of the new Anthurium differ from plants of the cultivar Atwelve in the following characteristics:

1. Plants of the new Anthurium are slightly shorter than plants of the cultivars Atwelve.
2. Plants of the new Anthurium have a slightly longer crop time than plants of the cultivar Atwelve.
3. Leaves of plants of the new Anthurium have shorter apices and are hence shorter than leaves of plants of the cultivar Atwelve.
4. Leaves of plants of the new Anthurium have more cordate bases than leaves of plant of the cultivar Atwelve.

5. Plants of the new Anthurium have thinner peduncles than plants of the cultivar Atwelve.
6. Spathes of plants of the new Anthurium are situated slightly closer to the foliage than spathes of plants of the cultivar Atwelve.
7. Spathes of plants of the new Anthurium are less deltoid, slightly longer and narrower, less puckered, with more truncate bases and more aristate apices than spathes of plants of the cultivar Atwelve.
8. Spathes of plants of the new Anthurium are almost flat whereas spathes of the plants of the cultivar Atwelve are often reflexed.
9. Front surfaces of spathes of plants of the new Anthurium are glossier and maintain glossiness longer than front surfaces of spathes of plants of the cultivar Atwelve.
10. Spathes of plants of the new Anthurium maintain color longer under high temperatures and/or high light conditions than spathes of plants of the cultivar Atwelve.
11. Rear surfaces of spathes of plants of the new Anthurium are lighter red in color and with very limited to no green coloration on the veins whereas rear surfaces of spathes of plants of the cultivar Atwelve have dark green veins.
12. Spathes of plants of the new Anthurium age more attractively as spathe color changes from red to brownish red with increasing green with age whereas spathes of plants of the cultivar Atwelve gradually fade in color with age.
13. Spadices of plants of the new Anthurium mature and age slower than spadices of plants of the cultivar Atwelve.
14. Spadix rachis of the new Anthurium is yellow-cream in color whereas spadix rachis of plants of the cultivar Atwelve is green in color.

Plants of the new Anthurium can be compared to the Anthurium cultivar A2, disclosed in U.S. Plant Patent No. 10,210. However, in side-by-side comparisons conducted in Altha, Fla., plants of the new Anthurium differ from plants of the cultivar A2 primarily in spathe color and also in the following characteristics:

1. Plants of the new Anthurium are shorter than plants of the cultivar A2.
2. Plants of the new Anthurium flower slightly earlier than plants of the cultivar A2.
3. Leaves of plants of the new Anthurium are slightly darker green and have more cordate bases than leaves of plants of the cultivar A2.
4. Plants of the new Anthurium have shorter and thinner peduncles than plants of the cultivar A2.
5. Spathes of plants of the new Anthurium are held more horizontal (less upright) and are situated slightly closer to the foliage than spathes of plants of the cultivar A2.
6. Spathes of plants of the new Anthurium are slightly broader and glossier than spathes of plants of the cultivar A2.
7. Rear surfaces of spathes of plants of the new Anthurium have very limited to no green coloration whereas rear surfaces of spathes of plants of the cultivar A2 have light green-colored veins.
8. Spathes of plants of the new Anthurium maintain color longer especially under high temperatures and/or high light conditions than plants of the cultivar A2.
9. Spathes of plants of the new Anthurium age more attractively as spathe color changes from red to brownish red with increasing green with age whereas spathes of plants of the cultivar A2 gradually fade in color with age.
10. Spadices of plants of the new Anthurium mature and age slower than spadices of plants of the cultivar A2.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Anthurium.

The photograph at the top of the first sheet comprises a top perspective view of a typical plant of 'Atwentyone' in a 10-cm container about 10.5 months after planting a single tissue culture-produced microcutting.

The photograph at the bottom of the first sheet comprises a close-up view of a typical young infloresence.

The photograph at the top of the second sheet comprises a close-up view of the upper surface of a typical leaf.

The photograph at the bottom of the second sheet comprises a close-up view of the lower surface of a typical leaf.

DETAILED BOTANICAL DESCRIPTION

The following observations and measurements were recorded on plants grown in Altha, Fla. in polycarbonate-covered greenhouses and under conditions which closely approximate those used in commercial horticultural practice. During the production of these plants, day temperatures ranged from 23 to 28° C., night temperatures ranged from 20 to 23° C., and light level ranged from 800 to 1,500 foot-candles. Plants used for this description were grown as single plants in 10-cm containers and were about 10.5 months from planting a tissue culture-produced microcutting. Fully developed plant structures and organs were used for the following observations and measurements unless otherwise indicated.

In the following description, color references are made to The Royal Horticultural Society Colour Chart except where general terms of ordinary dictionary significance are used. Numerical measurements represent averages from typical plants of 'Atwentyone'.

Botanical classification: Anthurium hybrid cultivar Atwentyone.

Parentage:

*Female parent.*—Proprietary Anthurium seedling selection identified as code No. 91-100-2, not patented.

*Male parent.*—Proprietary Anthurium seedling selection identified as code No. 91-9-32, not patented.

Propagation:

*Type.*—By tissue culture.

*Time to initiate roots.*—Summer: About 21 days with 25 to 30° C. soil temperatures. Winter: About 28 days with 22to 27° C. soil temperatures.

*Time to produce a rooted liner.*—Summer: About 16 to 18 weeks with 25 to 30° C. soil temperatures. Winter: About 18 to 20 weeks with 22 to 27° C. soil temperatures.

*Rooting characteristics.*—Primary roots thick, fleshy, dark pink to cream-colored with yellowish root cap. Lateral roots abundant and thick.

Plant description:

*Growth habit.*—Dwarf, relatively open, upright; between rounded and inverted triangle; moderate branching. Appropriate for 7.5 to 15-cm containers.

*Plant height, soil level to top of leaf canopy.*—About 17.4 cm.

*Plant height, soil level to top of inflorescences.*—About 18.5 cm.

*Plant diameter* (*area of spread*).—About 34.8 cm.

*Plant vigor.*—Vigorous.

*Crop time.*—About ten months are required to produce a finished plant in a 10 cm container from a single tissue culture-produced microcutting.

*Leaf description.*—Shape, young plants: Ovate; base, obtuse to truncate with cordate tendencies. Shape, mature plants: Ovate, slightly asymmetrical; apex, acuminate; base, cordate with some truncate tendencies. Venation: Prominent near base, less conspicuous near apex. Margin: Entire. Length, mature leaves: About 14.5 cm. Width, mature leaves: About 9.3 cm. Length to width ratio, mature leaves: About 1.6 to 1. Aspect: Midrib of most leaves approximately horizontal, leaf surface almost flat with lobes slightly curving upward. Texture/surface: Thick, leathery, glabrous; young leaves, glossy, older leaves, slightly glossy. Color: Young leaves, just after unfurling, upper surface: Darker and more green than 164A. Young leaves, just after unfurling, lower surface: Similar to 146A with some addition of 148A. Distal portions of midrib and leaf margin have some brownish anthocyanin coloration. Mature leaves, upper surface: Darker than 147A. Mature leaves, lower surface: Slightly darker than 147B. Mature leaves, venation, upper surface: Most of midrib and proximal portions of primary veins, 146A; remaining veins similar to or slightly lighter than surrounding tissue. Slight brownish Anthocyanin coloration sometimes present near petiole junction. Mature leaves, venation, lower surface: Proximal more than half of midrib, 144A. Remaining veins, slightly lighter or similar in color to the surrounding tissue.

*Petiole.*—Length, primary shoot: About 12.7 cm. Diameter, primary shoot, just below geniculum: About 3.3 mm. Geniculum length: About 1.2 cm. Geniculum diameter: About 3.9 mm. Petiole wings length, primary shoot: About 1.6 cm. Petiole wings width, primary shoot: About 4.8 mm. Color: Young leaves, just after unfurling: Front, between 148A and 199A, sometimes with a little 165A. Rear, between 146B and 148A with slightly grey-brown tint; geniculum, 146B. Mature leaves, winged area: Lighter than 147A. Mature leaves, above winged area: Front, 147B. Rear, between 146A and darker than 147B; distally lighter, 146B just below geniculum. Geniculum: Front, varies between 146A and 147B; rear, 144A.

Inflorescence description:

*Arrangement.*—Spathes with spadices held at or just below the foliar plane on relatively strong peduncles. Flowering structures arise from leaf axils. About 4.1 inflorescences per plant.

*Time of flowering, time to flower.*—Flowering year-round. Flowering commences about 8 months after planting of a tissue culture-produced microcutting.

*Inflorescence longevity.*—Spathes of plants of the new Anthurium are long-lasting. During the fall, spathes maintain red color and high gloss for about 2.5 to 3 months and gradually darken to brownish red with increasing amounts of green with subsequent development. Ornamental value is maintained for several months after maturity. After about 4.5 months, inflorescences are still attractive with spathes dark green with some brownish red undertones and contrasting red veins and margins.

*Fragrance.*—Relatively weak, somewhat unpleasant.

*Spathe.*—Shape: Between deltoid and ovate; apex, aristate; base, truncate, sometimes with cordate tendencies. Margin: Entire. Texture: Thick, leathery, glabrous, slightly puckered. Very glossy when young; maintains glossiness for an extended period of time. Rear surface less glossy than front surface. Aspect: Most, approximately horizontal, almost flat, not cupped. Length: About 6.8 cm. Width: About 5.9 cm. Length to width ratio: About 1.2 to 1. Color: Before unfurling: Varies between 46A, 53B, 53C and combinations thereof; slightly green veins and apex. Glossy. Just after unfurling: 53B; narrow, less than 1 mm wide margin, 53A. Mature, front surface: similar to but usually more pale than 53B; narrow, less than 1 mm wide margin, 53A. Mature, rear surface: Darker than 48A; narrow, less than 1 mm wide margin, 53A. Apex and sometimes portions of veins slightly green.

*Spadix.*—Length: about 4.3 cm. Diameter: About 7.9 mm. Shape: Columnar, slightly tapering in distal zone, mostly straight. Cross-section: Round; rachis, cream in color. Aspect: About 80 to 90° to spathe; usually in almost straight line with peduncle. Color: Just after spathe unfurling: Most similar to 160A with red dots in proximal zone from which pistils eventually emerge. Apex, close to 154A. The amount of red coloration increases with subsequent spadix development until it becomes the dominant color. Mature: Proximal zone, one or a combination of 51D, 50D and/or 49C with lighter, almost white, pistils. Distal zone, without pistils, close to 39A with some yellowish green at apex.

*Flowers.*—Quantity: About 7 to 9 per linear cm at mid-section. Pistil, mature, appearance: About 2 mm in length; protudes less than 0.5 mm beyond perianth; cross-section rectangular, about 1.2 by 1 mm; apex, flat. Stamen, mature, appearance: Do not protrude beyond perianth; flat, firmly pressed against pistils; about 1.2 by 0.7 mm in size. Pollen: Not observed to date. Seed development: Not observed to date.

*Peduncle.*—Length: About 13.4 cm. Diameter, just below spathe: About 3.3 mm. Stipe length: About 1.8 mm. Color: Young: Below spathe, 146A; proximally lighter; near base, between 144A and 146B. Mature: Front, below spathe, varies between 144A and 146B; proximally darker; near base, 146A. Rear, below spathe, varies between 146A and 146B; near base, 146A or darker.

Disease/insect resistance: Plants of the new Anthurium grown in commercial greenhouses have not shown any unusual susceptibility to pathogens or insects common to Anthurium.

It is claimed:

1. A new and distinct cultivar of Anthurium plant named 'Atwentyone', as illustrated and described.

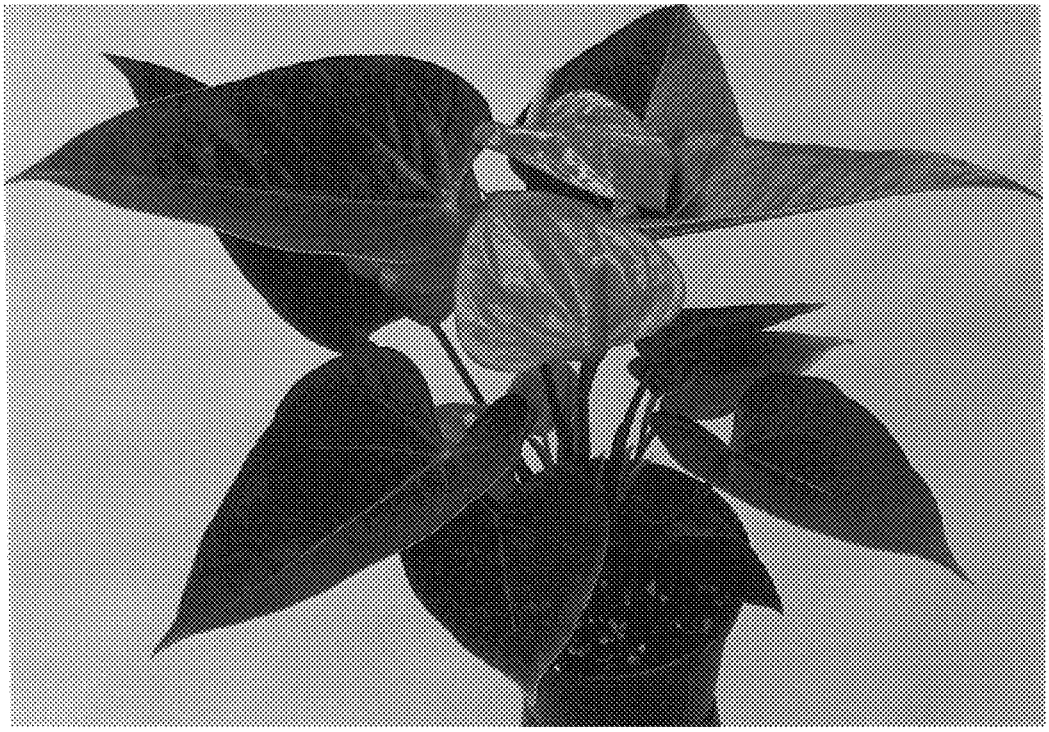
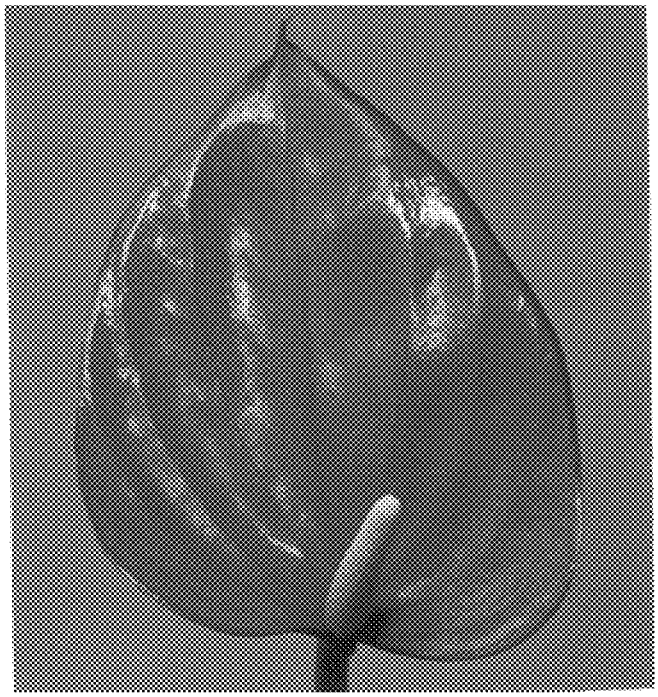

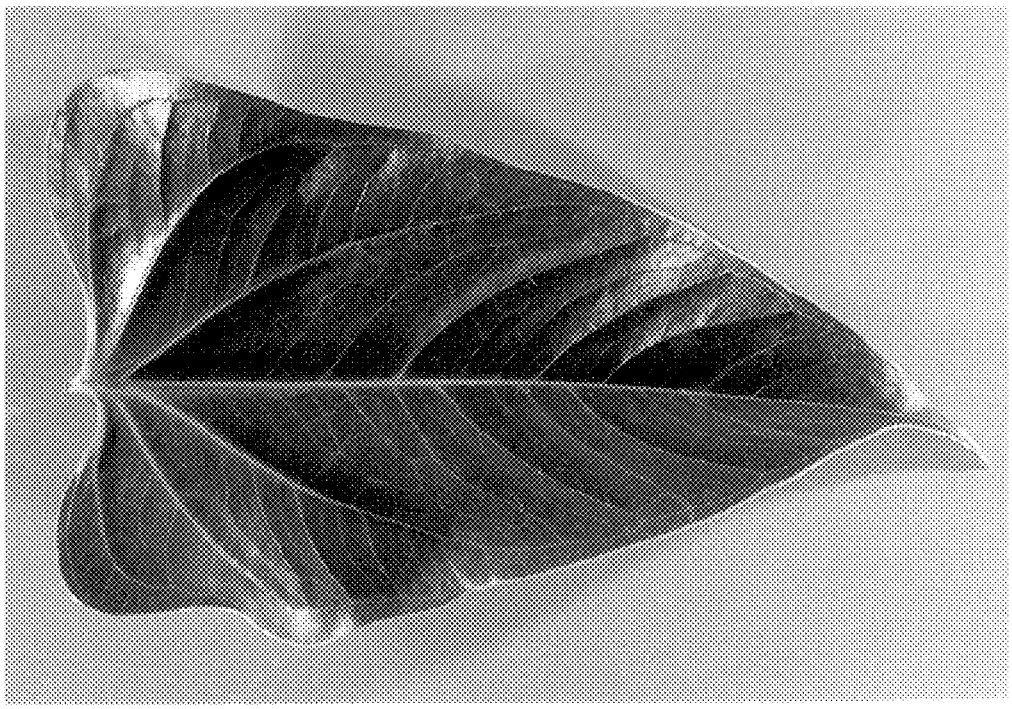
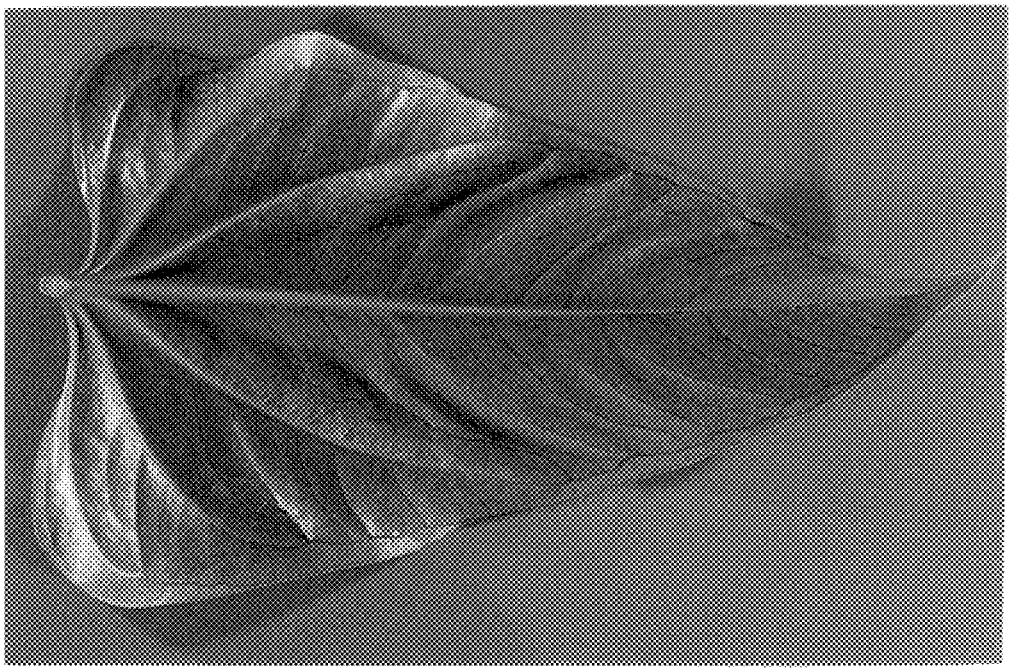

* * * * *